United States Patent [19]

Houdi

[11] Patent Number: 6,121,289
[45] Date of Patent: Sep. 19, 2000

[54] METHOD FOR ENHANCED BRAIN DELIVERY OF NICOTINIC ANTAGONIST

[75] Inventor: Abdulghani A. Houdi, Lexington, Ky.

[73] Assignee: Theramax, Inc., Lexington, Ky.

[21] Appl. No.: 09/169,150

[22] Filed: Oct. 9, 1998

[51] Int. Cl.[7] .......................... A61K 31/14; A61K 31/40; A61K 31/403; A61K 31/4188; A61K 31/445

[52] U.S. Cl. ........................ 514/315; 514/408; 514/386; 514/410; 514/416; 514/533; 514/642; 514/659

[58] Field of Search ................................. 514/315, 386, 514/408, 410, 416, 533, 642, 659

[56] References Cited

U.S. PATENT DOCUMENTS

| | | | |
|---|---|---|---|
| 2,831,027 | 4/1958 | Pfister, III et al. | 260/563 |
| 3,025,294 | 3/1962 | Huebner | 260/247.5 |
| 3,717,650 | 2/1973 | Herr et al. | 260/295.5 S |
| 3,731,683 | 5/1973 | Zaffaroni | 128/260 |
| 3,884,976 | 5/1975 | Bernauer et al. | 260/563 P |
| 3,979,494 | 9/1976 | Zaffaroni | 128/260 |
| 4,336,243 | 6/1982 | Sanvordeker et al. | 424/28 |
| 4,846,199 | 7/1989 | Rose | 131/329 |
| 4,891,380 | 1/1990 | Williams et al. | 514/353 |
| 5,198,459 | 3/1993 | Imperato et al. | 514/397 |
| 5,272,168 | 12/1993 | Imperato et al. | 514/397 |
| 5,316,759 | 5/1994 | Rose et al. | 424/10 |
| 5,519,044 | 5/1996 | Imperato et al. | 514/397 |
| 5,554,610 | 9/1996 | Williams et al. | 514/223.2 |
| 5,574,052 | 11/1996 | Rose et al. | 514/343 |
| 5,624,898 | 4/1997 | Frey, II | 514/12 |
| 5,691,365 | 11/1997 | Crooks et al. | 514/343 |
| 5,703,101 | 12/1997 | Rose et al. | 514/343 |
| 5,726,190 | 3/1998 | Rose et al. | 514/343 |
| 5,732,717 | 3/1998 | Watanabe et al. | 128/898 |
| 5,760,049 | 6/1998 | Viner | 514/291 |

OTHER PUBLICATIONS

Rose, "Nicotine Addiction and Treatment", *Annu. Rev. Med.* 47:493–507 (1996).

Paul Clarke, "Nicotine Dependence—Mechanisms and Therapeutic Strategies", *Biochem. Soc. Symp.* 59:83–95 (1993).

Jed Rose, Ph.D. et al., "Mecamylamine Combined With Nicotine Skin Patch Facilitates Smoking Cessation Beyond Nicotine Patch Treatment Alone", *Clinical Pharmacology & Therapeutics*, No. 1, 56:86–99 (1994).

Elan Corporation News Room, "Elan Reports on Nicotine Patch Studies and Its Late Stage Development Pipeline Status", Dublin Ireland, Nov. 24, 1998 (2 pages).

Toshiyasu Sakane et al., "Transport of Cephalexin to the Cerebrospinal Fluids directly From the Nasal Cavity", *J. Pharm. Pharmacol.* 43:449–451 (1991).

Forest S. Tennant, Jr., et al., "Clinical Evaluation of Mecamylamine for Withdrawal From Nicotine Dependence" *NIDA Research Monograph Series 49* "Problem of Drug Dependence 1983" Editor: Louis S. Harris, Ph.D., Mar. 1984 pp. 239–246.

Forest S. Tennant, Jr., et al., "Withdrawal from Nocotine Dependence Using Mecamylamine: Comparison of Three–Week and Six–Week Dosage Schedules", *Research Monograph Series 55* "Problem of Drug Dependence 1984" Editor: Louis S. Harris, Ph.D., Mar. 1984 pp. 291–297.

David H. Malin et al., "Nicotiine Abstinence Syndrome Precipitated by the Competitive Nicotinic Antagonist Dihydro–β–Erythroidine", *Pharmacology Biochemistry and Behavior*, No. 3, 60:609–613 (1998).

B.E. Hildebrand et al., "Behavioral Manifestations of the Nicotine Abstinence Syndrome in the Rat: Peripheral Versus Central Mechanisms", *Psychopharmacology* 129:348–356 (1997).

J. Prignot, "Pharmacological Approach to Smoking Cessation", *Eur Respir J* 2:550–560 (1989).

Kenneth S.E. Su et al., "Nasal Drug Delivery System of a Quaternary Ammonium Compound: Clofilium Tosylate", *Journal of Pharmaceutical Sciences* No. 9, 73:1251–1254 (1984).

H. El–Bizri et al., "Blockade of Nicotinic Receptor–Mediated Release of Dopamine From Striatal Synaptosomes by Chlorisondamine Administered in vivo", *Br. J. Pharmacol.* 111:414–418 (1994).

B.S. Clarke, "Chronic Central Nicotinic Blockade After a Single Administration of the Bisquaternary GanglionBlocking Drug Chlorisondamine", *Br. J. Pharmac.* 83:527–535 (1984).

B.S. Clarke et al., "Characterization of the Locomotor Stimulant Action of Nicotine in Tolerant Rates", *Br. J. Pharmac.* 80:587–594 (1983).

I.P. Stolerman, "Could Nicotine Antagonists be used in Smoking Cessation?", *British Journal of Addition* 81:(81)47–53 (1986).

J.E. Henningfield et al., "Stimulus Properties of nicotine in Animals and Human Volunteers: A Review", *Behavioral Pharmacology: The Current Status* pp. 443–449 (1984).

I.P. Stolerman, "Psychopharmacology of Nicotine: Stimulus Effects and Receptor Mechanisms" Handbook of Psychopharmacology, 19:421–465 (1975).

*Primary Examiner*—Phyllis G. Spivack
*Attorney, Agent, or Firm*—Burns, Doane, Swecker & Mathis, L.L.P.

[57] ABSTRACT

This invention provides methods of treatment of addiction to tobacco comprising intranasal administration of nicotinic antagonists.

4 Claims, No Drawings

METHOD FOR ENHANCED BRAIN DELIVERY OF NICOTINIC ANTAGONIST

FIELD OF THE INVENTION

This invention relates generally to a method for enhancing the delivery of nicotinic antagonists to the brain via the olfactory neural pathway, of a mammal in need of treatment with such drugs, by administering nicotinic antagonists intranasally. The present invention is particularly useful in a program to reduce the use of nicotine in patients attempting to quit smoking.

BACKGROUND

A great deal of evidence supports the view that people continue to smoke tobacco products, despite the widely publicized health risks associated with smoking, because of the reinforcing effects of nicotine. Substantial research literature suggests that nicotine contributes to and interacts with cigarette smoking behavior. It appears to be primarily the central actions of nicotine that tobacco smokers seek, and animal studies confirm the importance of central nicotinic actions in controlling behavior (see, e.g., Henningfield & Goldberg (1985) in *Behavioral Pharmacology*, Seiden & Blaster (eds), Alan R. Liss, N.Y., pp 443–449; Stolerman (1986) in *Handbook of Psychopharmacology*, Vol. 19, Iversen, Iversen, & Snyder (eds.), Plenum, N.Y.). Nicotine blockade therapy represents an alternative pharmacotherapeutic approach to tobacco use and cigarette smoking cessation (see, Stolerman, I. P. (1986) *Br. J. Addiction* 81:47–53; Clarke, P. B. S. (1993) *Biochem Soc. Symp.* 59:83–95). Nicotine blockade therapy is radically different from other approaches, since it should permit "pharmacological extinction" of smoking behavior. Smokers attempting to quit by this method would be administered a centrally-active nicotinic receptor antagonist while continuing to smoke. With every puff, the association between smoking and delivery of nicotine-associated reinforcement would be unlearned. This should reduce long-term craving and hence provide much lower relapse rates than other approaches.

Mecamylamine is a nicotinic antagonist, penetrates the blood-brain barrier, and blocks nicotinic effects both in the brain and periphery (see, Martin, B. R. et al. (1993) *Med. Chem. Res.* 2:564–577). Mecamylamine until recently was marketed as a hypotensive drug, Inversine® (Merck & Co.) to be administered in an oral dosage form. Preliminary studies of chronic mecamylamine administration as a potential aid to smoking cessation show that mecamylamine blocks the effect of nicotine and significantly reduces nicotine withdrawal symptoms, i.e., craving for cigarettes. The disadvantages of orally administered mecamylamine are those associated with its peripheral effects, resulting from its blockade of autonomic ganglia. These side effects, first noted when mecamylamine was used in the treatment of hypertension, include postural hypotension, orthostatic dizziness, nausea, vomiting, constipation, urinary retention, dryness of the mouth, abdominal cramps, decreased libido, impotence, blurred vision, fatigue and weakness. A major difficulty with prior attempts to use mecamylamine in smoking cessation programs has been persuading cigarette smokers to accept these unpleasant effects and at the same time give up the positively reinforcing effects of nicotine.

Chlorisondamine, a representative of quaternary ammonium compounds, is a bisquaternary noncompetitive ganglion-blocking drug which has been used clinically as an antihypertensive. Chlorisondamine does not readily cross the blood-brain barrier and does not block the behavioral effects of nicotine when administered systemically, although it blocks its peripheral effects (see, e.g., El-Bizri, H., & Clarke, P. B. S. (1994) *Br. J. Pharmacol* 111:414–418). Published reports indicate that injection of small doses of chlorisondamine directly into the brain block the behavioral effects of nicotine and a single brain injection completely blocked the effects of nicotine for several weeks (Clarke, P. B. S. & Kumar, R. (1983) *Br. J. Pharmacol.* 80:587–594). It has also been reported that a persistent central nicotinic blockade can also be achieved by giving the drug systemically in high doses in rats (Clarke, P. B. S. (1984) *Br. J. Pharmacol.* 83:527–535). As with mecamylamine, high doses of a ganglionic blocker such as chlorisondamine will produce serious and unpleasant side effects and it is not known whether systemic administration of centrally-active high doses would be safe in humans.

Therefore, in view of the aforementioned deficiencies attendant with prior art methods of nicotinic antagonists administration, it should be apparent that there still exists a need in the art for a safe and convenient method of administering nicotinic antagonists to patients at safe and effective doses.

SUMMARY OF THE INVENTION

Accordingly, a major object of the present invention is to provide a method for safely and conveniently administering nicotinic antagonists to a patient in need of such treatment, comprising intranasally administering an effective amount of nicotinic antagonists to prevent or treat symptoms of withdrawal from nicotine.

The objective of the present inventors is to improve the bioavailability of nicotinic antagonists by administering nicotinic antagonists via the nasal route. Intranasal delivery will improve drug bioavailability by direct absorption into the circulation avoiding extensive hepatic first-pass metabolism which significantly lowers the plasma and brain concentrations of nicotinic antagonists administered orally. Several reports (1–3) have shown that drugs achieve higher brain levels after intranasal administration than after intravenous administration, due to absorption via olfactory neural pathways. These studies support the notion that there is a direct pathway for transport of drugs from the nasal cavity to the brain.

1. Kenneth S. E. Su, Kristina M. Campanalc, and Christian L. Gries, "Nasal Drug Delivery System of a Quaternary Ammonium Compound: Clofilium Tosylate", *J. Pharmaceutical Sciences* 73:1251–1254 (1984)
2. T. Sakane, M. Akizuki, S. Yamashita, T. Nadai, M. Hahida, and H. Sezaki, The Transport of a Drug to a Cerebrospinal Fluid Directly from the Nasal Cavity: The Relation to the Lipophilicity of the Drug", *Chem. Pharm. Bull.* 39:2456–2458 (1991)
3. T. Sakane, M. Akizuki, M. Yoshida, S. Yamashita, T. Nadai, M. Hashida, and H. Sezaki, "Transport of Cephalexin to the Cerebrospinal Fluid Directly from the Nasal Cavity", *J. Pharmacy and Pharmacology* 43:449–451 (1991)

This method also permits a reduction in the dose required for the beneficial effect of nicotinic antagonists, leading to lower plasma concentrations of nicotinic antagonists and their metabolites, and therefore fewer side effects. Therefore, small doses of nicotinic antagonists can be administered which will result in fewer side effects, and the drug will be more tolerable and more effective, in a wider population of tobacco smokers engaged in treatment of their smoking addiction.

With the foregoing and other objects, advantages and features of the invention that will become hereinafter apparent, the nature of the invention is further explained in the following detailed description of the preferred embodiments of the invention and in the appended claims.

DETAILED DESCRIPTION OF THE PREFERRED EMBODIMENTS OF THE INVENTION

Thus, the present invention provides a novel method for the delivery of nicotinic antagonists to a patient in need of such treatment, comprising the intranasal administration of said nicotinic antagonists. This method offers significant clinical advantages over the prior art. More specifically, the present invention provides a safe, effective and convenient treatment for administering nicotinic antagonists to a patient in need of such treatment, which comprises the administration of said nicotinic antagonists intranasally, thus avoiding the side-effects associated with oral dosage forms. Specifically, smaller doses of nicotinic antagonists can be administered through the nasal route, thus resulting in fewer side effects. By using the method of the present invention, the drug will become more tolerable and more effective, particularly in treating tobacco smokers engaged in treatment of their smoking addiction.

The inventors have found that intranasal administration of nicotinic antagonists effectively results in absorption of said nicotinic antagonists both into plasma, and also directly into the central nervous system. Intranasal administration of nicotinic antagonists is as effective as oral administration, but may be conveniently and painlessly self-administered by the patient, and at lower doses, thereby allowing a decreased incidence of side effects.

In the context of the present invention, "nicotinic antagonists" are any compounds which block the action of nicotine at the nicotinic cholinergic receptor. Suitable nicotinic antagonists for use in the present invention include chlorisondamine, dihydro-β-erythroidine, hexamethonium, mecamylamine, pempidine, pentolinium salt, succinylcholine, tetraethylammonium, trimethaphan, and pharmaceutically acceptably salts thereof.

According to the present invention, nicotinic antagonists may be administered either as a free base, or in the form of a pharmaceutically acceptable salt thereof. Pharmaceutically acceptable salts of an acid group or an amino group include, but are not limited to, salts of organic carboxylic acids such as acetic, lactic, tartaric, malic, isothionic, lactobionic and succinic acids; organic sulfonic acids such as methanesulfonic, ethanesulfonic, benzenesulfonic and p-tolylsulfonic acids, and inorganic acids such as hydrochloric, sulfuric, phosphoric and sulfamic acids. Particularly preferred salts of nicotinic antagonists for use in the present invention include chlorisondamine dichloride, dihydro-β-erythroidine HBr, hexamethonium chloride, mecamylamine HCl, succinylcholine chloride, and tetraethylammonium chloride.

A still further aspect of this invention is a pharmaceutical composition of matter that comprises one or more nicotinic antagonists as described above, and/or pharmaceutically acceptable salts thereof, and pharmaceutically acceptable carriers therefor.

For therapeutic use in a smoking cessation program, one or more nicotinic antagonists, and/or salts thereof, can be conveniently administered in the form of a pharmaceutical composition comprising one or more nicotinic antagonists, or pharmaceutically acceptable salts thereof, and a pharmaceutically acceptable carrier therefor. Suitable carriers are well known to those skilled in the art and vary with the desired form and mode of administration of the pharmaceutical composition. Typically, the carrier may be a liquid, solution, suspension, gel, ointment, lotion, semi-solid, or vaporizable carrier, or combinations thereof. In a preferred embodiment, the carrier is a pharmaceutically acceptable aqueous carrier. Such compositions are prepared in accordance with accepted pharmaceutical procedures, for example, as described in *Remington's Pharmaceutical Sciences*, seventeenth edition, ed. Alfonso R. Gennaro, Mack Publishing Company, Easton, Pa., Eighteenth edition (1990), which is hereby incorporated by reference.

The compound of the invention or its salt may be formulated together with the carrier into any desired unit dosage form. Unit dosage forms such as solutions, suspensions, and water-miscible semisolids are particularly preferred.

Each carrier must be "acceptable" in the sense of being compatible with the other ingredients in the formulation and not injurious to the patient. The carrier must be biologically acceptable and inert. To prepare formulations suitable for intranasal administration, solutions and suspensions are sterilized and are preferably isotonic to blood.

The formulations may conveniently be presented in unit dosage form and may be prepared by any method known in the art. Such methods include the step of bringing the active ingredient into association with the carrier which itself may encompass one or more accessory ingredients. In general, the formulations are prepared by uniformly and intimately bringing into association the active ingredient with liquid carriers or finely divided solid carriers or both, and then if necessary shaping the product. Various unit dose and multidose containers, e.g., sealed ampules and vials, may be used, as is well known in the art (see *Remington's Pharmaceutical Sciences*, seventeenth edition, ed. Alfonso R. Gennaro, Mack Publishing Company, Easton, Pa., Eighteenth edition (1990)).

In addition to the ingredients particularly mentioned above, the formulations of this invention may also include other agents conventional in the art for this type of pharmaceutical formulation.

The present invention is also directed to a method for treating a patient addicted to tobacco smoking, by treating that patient with an effective amount of nicotinic antagonists intranasally. According to the present invention, the term "patient" will encompass any mammal requiring treatment with nicotinic antagonists, particularly a human patient addicted to tobacco and engaged in a smoking cessation program.

The dosage of nicotinic antagonists or pharmaceutically acceptable salts thereof in the compositions of the invention will vary depending on several factors, including, but not limited to, the age, weight, and species of the patient, the general health of the patient, the severity of the symptoms, whether the composition is being administered alone or in combination with other agents, the incidence of side effects and the like. The desired dose may be administered as 1 to 6 or more subdoses administered at appropriate intervals throughout the day. The compounds may be administered repeatedly over a period of months or years. Higher and lower doses may also be administered.

The daily dose may be adjusted taking into account, for example, the above-identified variety of parameters. For example, the nicotinic antagonist mecamylamine may be administered in an amount of up to about 5 mg/day. Preferably, the amount of mecamylamine administered will not exceed 1 mg/day. However, other amounts may also be administered.

To achieve good plasma concentrations, the nicotinic antagonists may be administered, for instance, by intranasal administration of an approximate 0.1 to 1M solution of the active ingredient, optionally in saline.

While it is possible for the active ingredient to be administered alone, it is preferably present as a pharmaceutical formulation. The formulations of the present invention comprise at least one active ingredient, as defined above, together with one or more acceptable carriers thereof and optionally other therapeutic agents.

The above method may be practiced by administration of the compounds by themselves or in a combination with other active ingredients in a pharmaceutical composition. Other therapeutic agents suitable for use herein are any compatible drugs that are effective by the same or other mechanisms for the intended purpose, or drugs that are complementary to those of the present agents, e.g., other antidepressants, particularly tricyclic antidepressants. The compounds utilized in combination therapy may be administered simultaneously, in either separate or combined formulations, or at different times than the present compounds, e.g., sequentially, such that a combined effect is achieved. The amounts and regime of administration will be adjusted by the practitioner, by preferably initially lowering their standard doses and then titrating the results obtained. The therapeutic method of the invention may be used in conjunction with other therapies as determined by the practitioner.

Having now generally described this invention, the same will be better understood by reference to certain specific examples, which are included herein for purposes of illustration only and are not intended to be limiting of the invention or any embodiment thereof, unless so specified.

EXAMPLE 1

In these experiments we will determine the bioavailability of nicotinic antagonists after nasal administration and compare it to that after intravenous administration.

The nasal absorption of nicotinic antagonists may be measured using an in vivo technique in rats. Rats are fasted overnight prior experimentation. Surgical procedures are performed under equithesin anesthesia (3 ml/kg, i.p.), an incision is made in the neck, and the trachea cannulated with polyethylene tubing (PF-260). A closed end tube is inserted through the esophagus to the posterior part of the nasal cavity to prevent drug from entering the esophagus. The nasopalatine passage is closed with an adhesive agent to prevent drainage of the drug from the nasal cavity to the mouth.

The jugular vein and femoral artery are cannulated with polyethylene tubing for intravenous drug administration and intra-arterial blood sampling.

Solutions of nicotinic antagonists, including chlorisondamine dichloride, dihydro-$\beta$-erythroidine HBr, hexamethonium chloride, mecamylamine HCl, succinylcholine chloride, and tetraethylammonium chloride are prepared in water and administered through the right nostril using a microsyringe. For intravenous administration, the same dose of the drug is injected into the jugular vein. Blood samples after nasal or intravenous drug administration are collected before and at 2, 15, 30, 60 and 120 min after drug administration, centrifuged, and serum removed and stored ($-80°$ C.) until analysis. Cerebrospinal fluid (CSF) is obtained in the following manner: an incision is made in the skin over the occipital bone and the first layer of the muscle is cut. CSF is collected by cisternal puncture using a 25-gauge needle connected via PE-50 tubing. At specific time points 100 $\mu$l CSF is collected, frozen and stored ($-80°$ C.) until analysis.

Bioavailability of nasally administered drug is calculated by comparing the plasma and CSF drug concentrations between nasal and intravenous delivery routes and expressed as a percentage of the intravenous bioavailability.

EXAMPLE 2

Nasal Spray Solution

| | |
|---|---|
| Mecamylamine HCl | 1 mg |
| Isotonic Saline | 30 ml |

The mecamylamine HCl is dissolved in the sterile isotonic saline and the pH is adjusted to about 7.4. The solution is placed in a nasal administrator designed to deliver 0.1 ml of spray for each application. One spray in each nostril will deliver a total of 0.1 mg of mecamylamine HCl.

EXAMPLE 3

Nasal Gel (Aqueous)

| | |
|---|---|
| Mecamylamine HCl | 10 mg |
| Methocel | 3 gm |
| Water | 100 ml |

Approximately 7 g of water is heated to 80° C., and the methocel is dispersed in it with stirring. The mecamylamine HCl is dissolved in 30 ml of water at 80° C., and the solution is mixed with the methocel dispersion. The resultant mixture is allowed to stand at room temperature for 3 hours. The gel is placed in an ointment tube equipped with a fine orifice and is applied in the nasal nares with a finger or cotton tipped applicator.

While the invention has been described and illustrated herein by references to various specific material, procedures and examples, it is understood that the invention is not restricted to the particular material, combinations of material, and procedures selected for that purpose. Numerous variations of such details can be implied and will be appreciated by those skilled in the art.

What is claimed is:

1. A method for treating addiction to tobacco comprising intranasally administering to a patient in need of such treatment a pharmaceutical composition comprising a nicotinic antagonist, or a pharmaceutically acceptable salt thereof, and a pharmaceutically acceptable carrier therefor.

2. A method according to claim 1 wherein the nicotinic antagonist is selected from the group consisting of dihydro-$\beta$-erythroidine, mecamylamine, pempidine, succinylcholine, tetraethylammonium, trimethaphen, and pharmaceutically acceptable salts thereof.

3. A method according to claim 2, wherein the carrier is aqueous.

4. A method according to claim 1, wherein the nicotinic antagonist is selected from the group consisting of chlorisondamine, hexamethonium, pentolinium, and pharmaceutically acceptable salts therof.

* * * * *